United States Patent [19]

Welsh

[11] Patent Number: 5,853,664
[45] Date of Patent: Dec. 29, 1998

[54] FLOW MODULATION FOR FACILITATING DETECTOR IGNITION

[75] Inventor: Paul B. Welsh, Wilmington, Del.

[73] Assignee: Hewlett-Packard Company, Palo Alto, Calif.

[21] Appl. No.: 948,880

[22] Filed: Oct. 10, 1997

Related U.S. Application Data

[62] Division of Ser. No. 670,033, Jun. 25, 1996, Pat. No. 5,723,091.

[51] Int. Cl.[6] .............................. B01D 15/08; G01N 27/00
[52] U.S. Cl. .............................. 422/54; 422/89; 422/105; 436/154; 436/161; 73/23.1; 55/18; 55/20; 55/21; 55/67; 55/197; 55/386
[58] Field of Search .................................. 422/54, 89, 91, 422/105, 108, 109; 436/154, 161; 73/23.1; 55/20, 21, 197, 18, 67, 208, 270, 386

[56] References Cited

U.S. PATENT DOCUMENTS

| | | | |
|---|---|---|---|
| 4,059,994 | 11/1977 | Annino et al. | 73/23.1 |
| 4,311,664 | 1/1982 | Zaremba et al. | 422/54 |
| 4,346,055 | 8/1982 | Murphy et al. | 422/54 |
| 4,650,499 | 3/1987 | Scott | 55/18 |
| 4,869,876 | 9/1989 | Arfman et al. | 422/89 |
| 4,871,453 | 10/1989 | Kumar | 210/198.2 |
| 4,873,862 | 10/1989 | Scott et al. | 73/23.1 |
| 4,883,504 | 11/1989 | Gerstel | 55/67 |
| 4,883,958 | 11/1989 | Vestal | 250/288 |
| 4,948,389 | 8/1990 | Klein et al. | 55/20 |
| 4,976,750 | 12/1990 | Munari | 55/21 |
| 4,994,096 | 2/1991 | Klein et al. | 55/20 |
| 4,999,162 | 3/1991 | Wells et al. | 422/54 |
| 5,108,466 | 4/1992 | Klein et al. | 55/20 |
| 5,163,979 | 11/1992 | Patrick et al. | 55/21 |
| 5,205,845 | 4/1993 | Sacks et al. | 55/197 |

OTHER PUBLICATIONS

Gallagher, M. M., et al: "Selectivity Enhancement Of A Metal–Sensitive Flame Ionization Detector For Capillary Gas Chromatography," Journal Of High Resolution Chromatography, vol. 13, No. 10, 1 Oct. 1990.

*Primary Examiner*—Harold Y. Pyon
*Attorney, Agent, or Firm*—Mark Z. Dudley

[57] ABSTRACT

Method for the analysis of one or more analytes present in a sample carried in a first fluid. The first fluid is combined with a first detector fluid and a second detector fluid to provide a fluid mixture which flows across the surface of an igniter. The analytes are ionized by means of an ionization process. The ion current is collected and measured at a collector electrode adjacent to the igniter. The flow of at least one of the first detector fluid and second detector fluid is modulated during an ignition sequence according to predetermined criteria so as to facilitate flame ignition.

8 Claims, 9 Drawing Sheets

FLOW MODULATION FOR FACILITATING DETECTOR IGNITION

CROSS REFERENCE TO RELATED APPLICATION

This is a divisional of application Ser. No. 08/670,033 filed on Jun. 25, 1996, now U.S. Pat. No. 5,723,091.

FIELD OF THE INVENTION

The present invention relates generally to gas chromatography, and in particular to the operation of a flame-based detector.

BACKGROUND OF THE INVENTION

Flame-based detectors are used in the field of chromatography for the detection of specific constituent components (i.e., analytes) of a sample that are present in a fluid stream. Two such detectors are the flame ionization detector (FID) and the flame photometric detector (FPD).

Flame ionization detectors operate by burning the material to be analyzed so as to form ions. When used with a gas chromatograph, the gases eluting from a separation column are mixed with a flammable gas such as hydrogen and passed through a jet. An energy source, such as an electrical heating current carried by a resistive heating wire embedded in the igniter, heats the fluid stream to an ignition condition, whereupon a flame is established. Air is introduced at the periphery of the jet so as to form a stable flame when the jet is ignited. A collector tube is positioned adjacent the jet, and an electrometer is connected in a circuit with the collector and the jet so as to collect the ions formed in the flame. A current is produced for measurement by the electrometer in proportion to the rate at which the ions are collected.

Although the FID ignition depends upon an adequate flow of air, the flame will not ignite at normal operating air flow rates, and therefore it is known to provide a fixed reduction in the air flow (typically, about 70%–80%) received by the detector so as to encourage ignition. One prior art thermionic detection technique therefore attempts to divert the air stream from the detector during the ignition of the flame. One prior art flame detector utilizes an "air dump" valve which is manually activated by the operator. The air dump diverts part of the air flow to the atmosphere when the ignition is attempted.

The flame photometric detector is ignited in a fashion similar to that of the flame ionization detector. However, because an FPD uses a flame that is substantially enriched with hydrogen rather than air, ignition in an FPD is typically aided by increasing the air flow, while the hydrogen flow is held constant, to prevent an explosion when the flame is ignited. Some prior art thermionic detection techniques therefore attempt to increase the air stream delivered to an FPD when an ignition is attempted.

However, the aforementioned approaches have significant drawbacks. The addition of a valve to divert or increase air flow is also more costly and complex to implement than is desirable. The practice of diverting or increasing one or more of the gas flows is typically controlled by an operator by manual intervention, which is cumbersome, inconvenient, and subject to error. Apparatus for providing automation of the diversion of a gas flow has been disclosed; see, for example, U.S. Pat. No. 4,346,055.

Even repeated attempts at ignition (or re-ignition) can be unsuccessful at times when the operating conditions of the chromatograph are marginally suitable, or unsuitable, for ignition. Furthermore, the operator is typically unaware of the optimal conditions that are required for ignition, thus compounding the difficulty. The operator typically must make repeated attempts at ignition before successful ignition occurs, and does so without knowledge of the optimal the conditions for ignition, and therefore the ignition procedure can be significantly longer and more arduous than is acceptable. These drawbacks are also found in the aforementioned automated flow diversion apparatus.

The aforementioned drawbacks are even more bothersome during an attempt to re-ignite a detector during a flame-out condition that has arisen during an ongoing operation of the chromatograph. For example, the loss of a flame during an analytical run requires an immediate reignition in order to achieve a quick resumption of the operation of the detector. Otherwise, the results from a significant amount of the analytical run will be compromised.

SUMMARY OF THE INVENTION

This invention provides a method and apparatus for an improvement in the flame-based detection of one or more analytes in a sample.

In a first preferred embodiment of the present invention, an analytical instrument for detecting the presence of an analyte in a first fluid may be constructed to include a pneumatic manifold for providing a selectable flow of at least one of a plurality of fluids, said plurality including the first fluid, a first detector fluid, and a second detector fluid; a pneumatic controller, responsive to a control signal, for causing said selectable flow to be modulated; a flame-based detector, operably connected to the pneumatic manifold for receiving the modulated selectable flow, and a programmable computer for providing said control signal in a predetermined ignition sequence so as to effect said modulation according to predetermined flow modulation criteria that facilitate ignition.

DETAILED DESCRIPTION OF THE PREFERRED EMBODIMENTS

The apparatus and methods of the present invention may be employed in particular to improve the detection of an analyte that may be present in a variety of fluids. Gases are the preferred fluids according to the practice of the present invention, and therefore the following description of the invention will include a description of the arrangement, construction, and operation of pneumatic devices, and is directed to the control of a plurality of gaseous streams in a detector in a gas chromatographic analytical system (hereinafter, a chromatograph). However, for the purposes of the following description, the term "pneumatic" will also be considered to refer to all types of fluids.

Further examples that are particularly benefited by use of the present invention include supercritical fluid chromatography and high-pressure gas chromatography (HPGC). However, it should be understood that the teachings herein are applicable to other analytical instruments, including liquid chromatographs, high-pressure liquid chromatographs (HPLC), clinical analyzers, flow-injection analyzers, laboratory water purification systems, syringe-type reagent dispensers, manual and automated solid phase extraction (SPE) instruments, supercritical fluid extraction (SCF) instruments, stopped-flow spectrophotometers, automated protein or nucleic acid sequencers, and solid phase protein or nucleic acid synthesizers.

Figure 1:
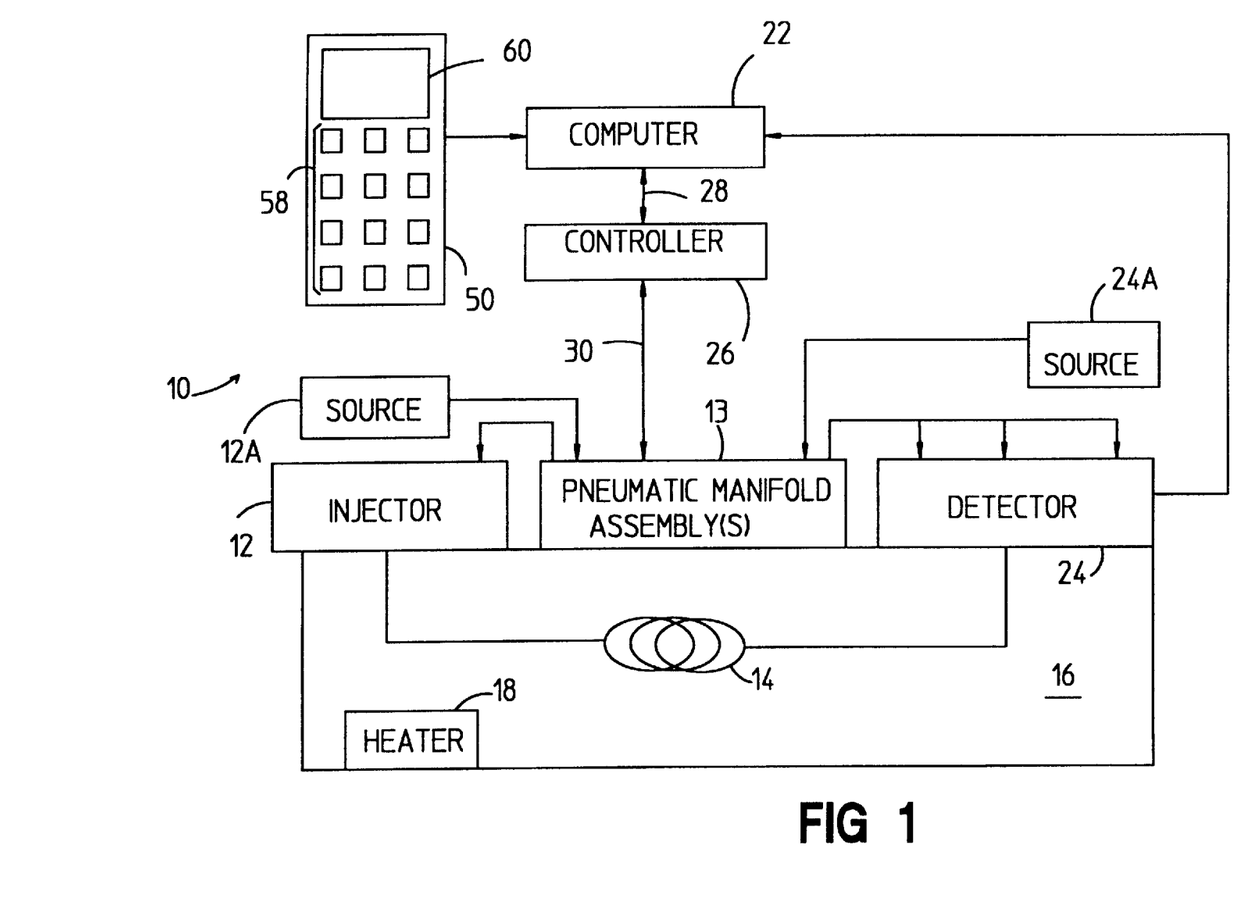
FIG. 1 is simplified schematic representation of a chromatograph constructed according to the present invention.

A new and novel analytical instrument is shown in FIG. 1 and is generally designated chromatograph 10. In the preferred embodiment, the chromatograph 10 is a Hewlett-Packard HP6890 gas chromatograph. In order to perform a chromatographic separation of a given sample compound, a sample is injected with a pressurized carrier gas by means of an injector 12. The carrier gas supplied to injector 12 is provided from a source 12A through one or more pneumatic manifold assemblies 13, each of which serves in part to control and redirect a plurality of gas flows, including the carrier gas and a plurality of detector gasses of appropriate types, such as air, hydrogen, and make-up gas. The detector gases are provided from respective sources (one such source 24A is shown) to the pneumatic manifold assembly 13. Suitable fluid-handling devices such as valves, sensors and the like in the pneumatic manifold assembly 13 are operated under the control of the computer 22 by a way of control signals provided on a data and control lines 28, 30. For example, the pneumatic controller 26 effects control of, among other things, fluid flow rate, fluid pressure, fluid flow regulation, and the continuity or discontinuity of flow. As further example, the time during which a particular valve in the pneumatic manifold assembly 13 will remain open and closed in relation to control signals received on the data and control line 28 and in accordance with certain operating conditions of the chromatograph 10. The control and data line 30 also allows the return of sense information from suitable sensors and signal-interface electronics that are provided in the pneumatic manifold assembly 13. Accordingly, the computer 22, pneumatic controller 26, and pneumatic manifold 13 may be operated to effect a modulation of any of the aforementioned gas flows, either individually or in combination.

A column 14 is positioned within an oven 16. The carrier gas/sample combination passing through column 14 is exposed to a temperature profile resulting in part from the operation of a heater 18 within oven 16. During this profile of changing temperatures, the sample will separate into its components primarily due to differences in the interaction of each component with the column 14 at a given temperature. As the separated components exit the column 14, they are detected by the detector 24.

As the components exit column 14 they are detected by a flame-based detector (hereinafter, detector) 24. In particular, and in accordance with a feature of the present invention, the pneumatic controller 26 modulates the flow of one or more of the detector gases that are provided to the detector 24 during an ignition sequence, as will be described below.

Computer 22 maintains overall control of all systems associated with gas chromatograph 10. It will be recognized that any particular gas chromatograph may include more systems than those described in relation to the present invention. It will also be understood that although computer 22 is shown as a single block, such computer includes a central processing unit and all associated peripheral devices, such as random access memories, read-only memories, input/output isolation devices, clocks and other related electronic components. In the preferred embodiment, the central processor used in computer 22 is a microprocessor. As such, computer 22 includes a memory in which information and programming can be stored and retrieved by known methods. However, it will be appreciated that the programmed control of pneumatic controller 26 can be implemented by other computing means, such as an embedded microprocessor or dedicated controller circuit incorporated in the pneumatic controller 26. Also, the programming associated with computer 22 that is utilized in relation to the present invention will be readily understood from the description herein.

An electronic control panel 50 is shown to include at least two main input/output components, namely a keypad 58, and a display 60. By monitoring the operation of the chromatograph 10 by signals from certain components, such as the detector 24, the computer 22 can initiate and maintain certain functions required for an analytical run. Consequently, indicating or prompt messages can be generated by computer 22 and displayed on display 60. Operating commands and other information are entered into computer 22 by way of keypad 58. One particular data type is detector ignition setpoint values and one particular operating command is a detector ignition command, both of which may be prompted by messages displayed on display 60 and the requisite command or data are entered through keypad 58. Another particular type of data is a detector ignition lit offset value, which may be acknowledge by messages displayed on display 60 and modified by commands and data entered through keypad 58. The ensuing ignition sequence which relates to the present invention is then automatically provided under control of the computer 22 as described below in reference to FIGS. 4 and 5.

Figure 2:
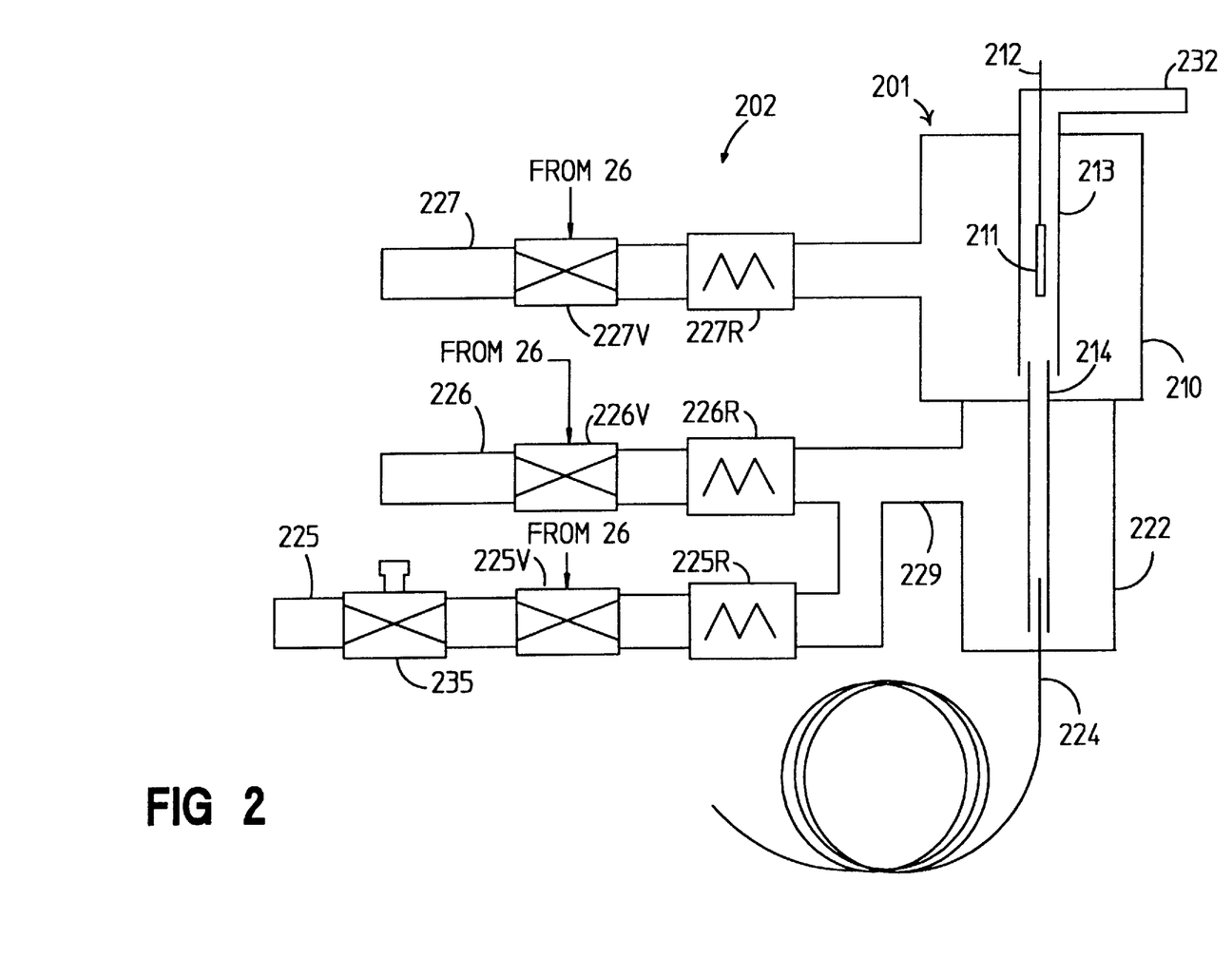
FIG. 2 is a simplified cross-sectional illustration of a portion of the chromatograph of FIG. 1, showing a first configuration of a pneumatic control section and a flame-based detector constructed according to the present invention.
Figure 3:
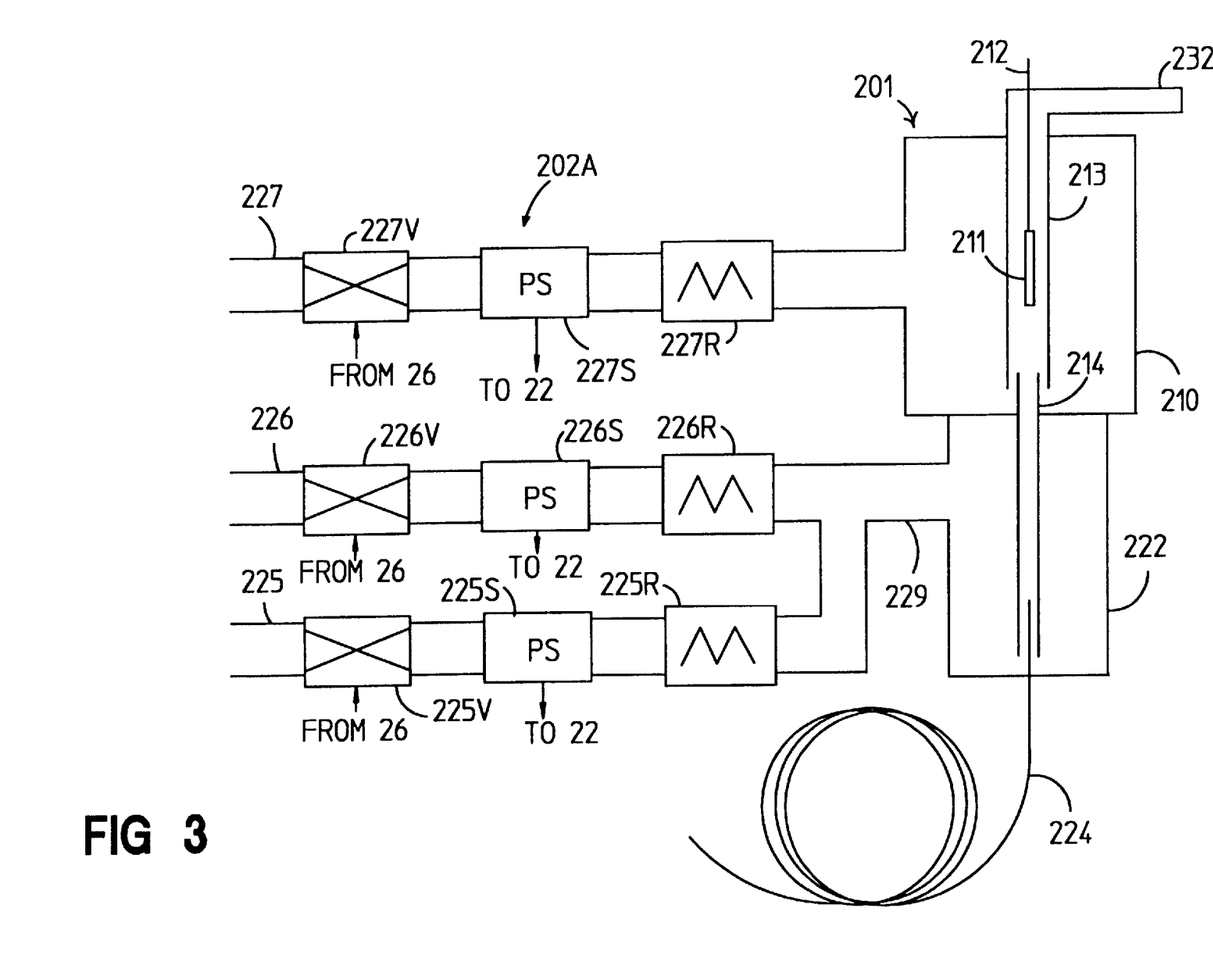
FIG. 3 is a simplified cross-sectional illustration of the portion of the chromatograph of FIG. 1, showing a second configuration of the pneumatic control section.

The control of one or more fluid flow characteristics is provided as shown in FIGS. 2 and 3. In the embodiments illustrated in FIGS. 2 and 3, the computer 22 controls the flow of the make-up fluid, the first fluid, the first detector fluid, and the second detector fluid by transmitting an appropriate signal to the pneumatic controller 26, which in turn provides respective signals to a respective valve in the pneumatic manifold assembly 13 to increase or decrease the amount of fluid flowing therethrough to the detector 201. In particular, the fluid flow control in the embodiment illustrated in FIG. 3 is preferably provided via electronic pneumatic control (EPC). For further details of electronic pneumatic control techniques, one may consult, for example, Klein, et al., U.S. Pat. Nos. 4,994,096 and 5,108,466, the disclosures of which are incorporated herein by reference.

FIG. 2 shows a schematic illustration of a first preferred embodiment of a detector 201 preferably constructed as a FID and a pneumatic control section 202 that is best suited for operation in a non-EPC configuration. The detector 201 constructed to include an igniter 211, an ignition line 212, and a collector electrode 213. The igniter 211 and the collector electrode 213 are aligned in the interior of a jet 214 that is mounted in a passageway defined by a fluid-directing structure 210. An electronic power supply (not shown) provides a controlled amount of electrical current or voltage on the ignition line 212 to cause a selectable amount of heat in the igniter 211. In response, the fluid flow in the proximity of a jet 214 achieves an elevated temperature and is ignited. A vent tube 232 allows the combustion and further passage of the fluid mixture from the detector 201. The collector electrode 213 is electrically connected to an ion current measurement device (not shown) such as an electrometer which is used to measure the magnitude of ionization current that flows from the jet 214 to the collector electrode 213. The resulting ion current is measured to provide a chromatogram.

A fluid mixing structure 222 communicates with the fluid-directing structure 210 for directing the following fluids toward the igniter 211: a first fluid supplied on a first fluid supply line 224, a make-up fluid supplied on a make-up fluid line 225, a first detector fluid supplied on a first detector fluid line 226, and a second detector fluid supplied on a second detector fluid line 227. Preferably, the first fluid line 224 is integral with the column 14 and hence the first fluid comprises a heated, gaseous combination (under pressure) of the sample that is to be analyzed and a carrier gas. The make-up fluid also preferably comprises carrier gas; the first detector fluid comprises pressurized hydrogen ($H_2$) gas; and the second detector fluid comprises air at ambient pressure and temperature. The make-up fluid and the first detector fluid are combined via a conduit 229 connected between the fluid mixing structure 222, the make-up fluid line 225, and the first detector fluid line 226. Also included are a make-up fluid pressure regulator 235, a make-up fluid valve 225V, and a make-up fluid restrictor 225R; first detector fluid valve 226V and restrictor 226R; and second detector fluid valve 227V and restrictor 227R. In the instance that the detector 201 is constructed as a FID, it is contemplated that a predetermined pneumatic volume is provided in the second detector fluid line 227 between the valve 227V and the restrictor 227R. (In the alternative instance that the detector 201 is constructed as a FPD, it is contemplated that a predetermined pneumatic volume would be provided in the first detector fluid line 226 between the valve 226V and the restrictor 226R.) The valves 225V, 226V, and 227V are preferably solenoid valves that are subject to the control of the pneumatic controller 26 as will be described in greater detail below.

FIG. 3 illustrates an alternative embodiment 202A of the pneumatic control section 201 of FIG. 2 that is best suited for operation as an EPC configuration. That is, in FIG. 3, the valves 225V, 226V, and 227V are preferably provided in the form of proportional valves that are subject to the control of the pneumatic controller 26 according to signals received by the computer 22 from sensors 225S, 226S, and 227S, as will be described in greater detail below. Preferably, such sensors are pressure sensors that provide sense signals indicative of the respective pressures in the make-up fluid line 225, first detector fluid line 226, and second detector fluid line 227.

In the embodiment illustrated in FIG. 3, sensors 225S, 226S, 227S each sense a particular fluid parameter, such as fluid pressure or fluid flow, and transmits a feedback signal representative of such parameter to the computer 22. By monitoring the sense signals from sensors 225S, 226S, 227S, the computer 22 can effect near-instantaneous alteration of the flow of each fluid that is provided to the detector 201 at any desired time.

In the preferred embodiment of the computer 22, the procedures necessary to set up or operate chromatograph 10, so that a particular gas chromatographic separation test or analytical run can be conducted, are automated. The contemplated automation allows the operator to program events using programming via a table of fluid flow setpoints, a run table, and by clock time programming. A plurality of timed events may be programmed in each run table for execution during an analytical run. Run time programming allows certain setpoints to change automatically during a run as a function of the chromatographic run time. For example, an event such as detector ignition may be programmed to occur prior to injection. Such programming is contemplated as being applicable to the operation of the pneumatic controller, and particularly to the control of at least one of the first detector fluid flow and the second detector fluid flow.

Figure 4:
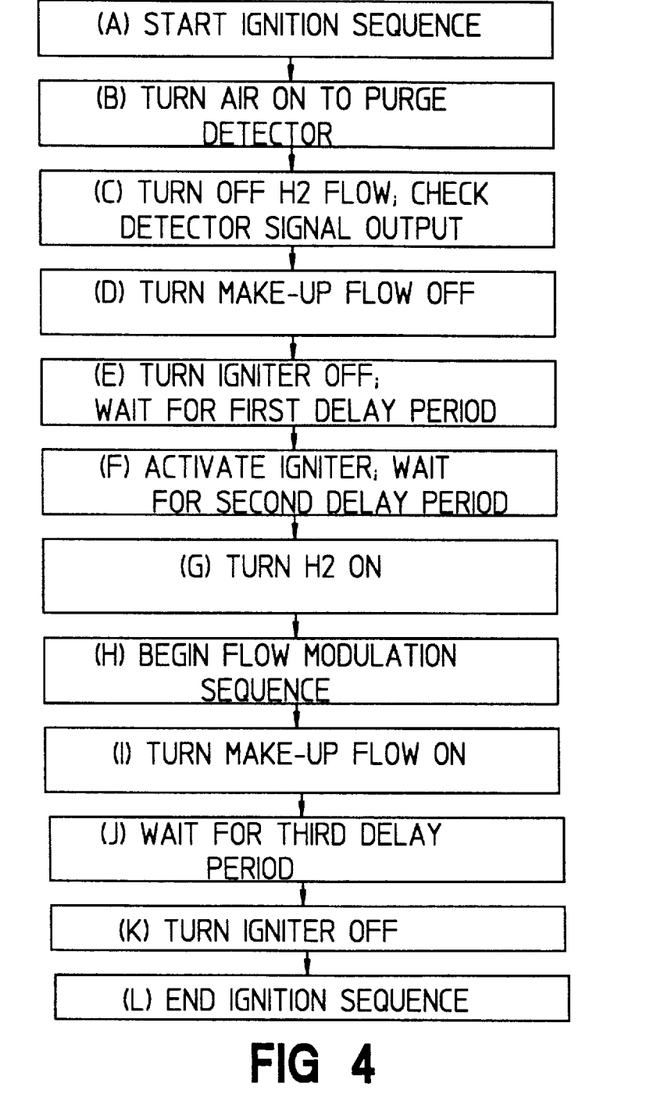
FIGS. 4 and 5 are representations of successive steps that are employed in an ignition sequence provided in the chromatograph of FIG. 1.
Figure 5:
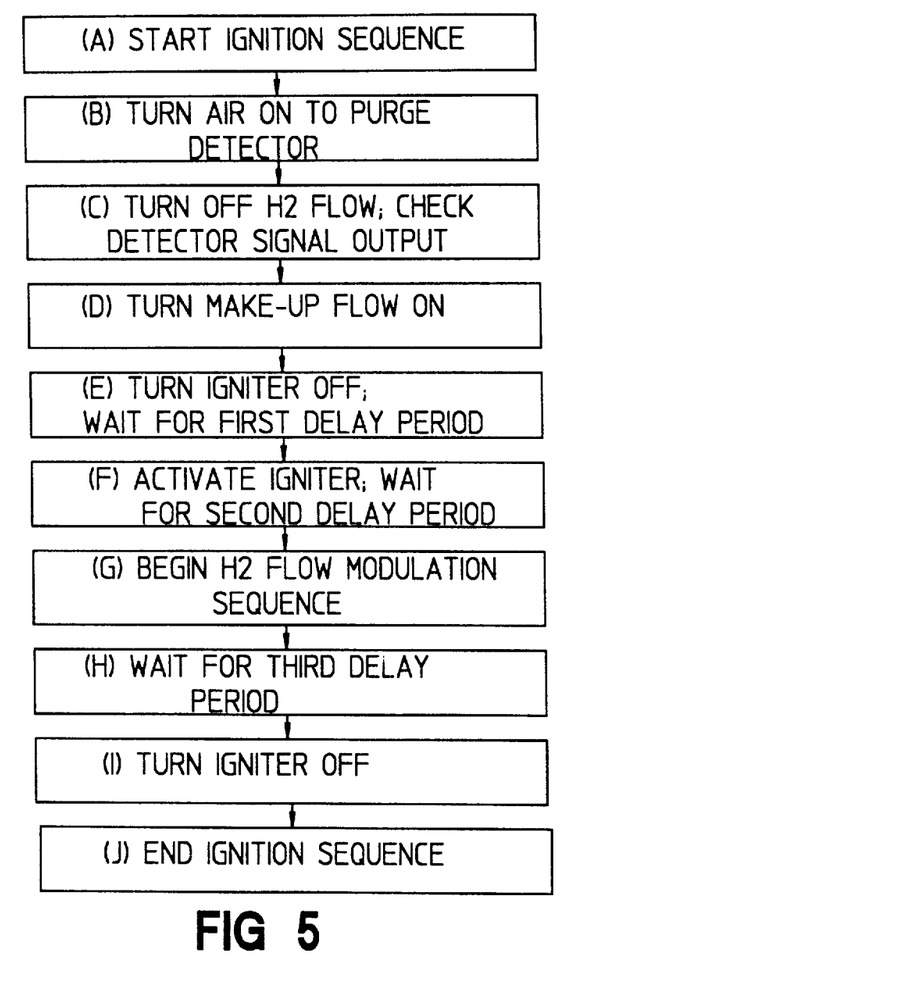

Certain programmed steps effected by computer 22 in controlling the operation of the pneumatic controller 26, which relate to and are in accordance with the present invention, are illustrated in FIGS. 4 and 5. In the preferred embodiment, the operator may enter data regarding the operation of the pneumatic controller 26 into the computer 22 by use of the keypad 58. The computer 22 operates to store the entered information into memory. The data thus entered may include one or more commands that are to be implemented immediately, or if necessary, the entered data may be stored in the form of one or more tables for later access. For example, the programmed events may be arranged in order of execution time in a run table. Text denoting the characteristics of each event may be displayed on the display 60.

In the embodiments illustrated in FIGS. 2 and 3, individual fluid streams combine to form a fluid mixture that is restricted to pass the igniter 211 and the collector electrode 213. The flow characteristics and the composition of the fluid mixture that passes the igniter 211 will determine the success or failure of the ignition mechanism that occurs at the igniter 211. Hence, in a departure from the prior art, the content of the fluid mixture is temporarily altered during certain steps in an ignition sequence, so as to favor the ignition mechanism and thereby facilitate ignition. Specifically, the flow of at least one of the fluid streams is modulated to effect either an increase or decrease in the fluid flow.

Accordingly, and in a particular feature of the present invention, a particular modulation of the flow of the first or second detector fluid during an ignition sequence has been found to facilitate detector ignition. Such ignition has been successful in instances that may otherwise be unsuccessful due to the influence of the content and other characteristics of the fluid mixture. In the preferred embodiment, and as illustrated in FIGS. 4 and 5, either the air flow rate or the hydrogen flow rate is modulated during a portion of the ignition sequence. The implementation of the modulation will differ slightly according to whether the embodiments of FIG. 2 or FIG. 3 are provided. Because the flow through the solenoid valves shown in the configuration in FIG. 2 can only be turned on or off, rather than varied continuously, a modulated flow is preferably achieved by cycling the appropriate valve (valve 227V or FID, valve 226V for FPD) on and off, starting at a low duty cycle and increasing it (preferably at a fixed frequency) until full flow is attained. In the configuration illustrated in FIG. 3, the contemplated EPC achieves a modulated flow by opening the appropriate valve (valve 227V for FID, valve 226V or FPD) in a continuous ramp, starting at a low value and increasing it until full flow Is attained.

In an instance of non-EPC control, the second detector fluid flow is best modulated by a solenoid valve according to the practice of:

a) fixing the flow duty cycle and varying the frequency of modulation;

b) fixing the frequency of modulation and varying the flow duty cycle; or c) varying both the flow duty cycle and the frequency of modulation.

Preferably, a fixed frequency option is selected because it is the easiest to implement in firmware resident in the computer 22. The preferred frequency of modulation is chosen to offer:

d) for all operating conditions, a predetermined range of duty cycles that will result in ignition, and e) for the most severe conditions (such as may be found during a very high second detector fluid flow and when helium is used as the make-up gas), the greatest span of duty cycles which will result in ignition.

In another feature of the present invention, the aforementioned criteria may be applied to a particular chromatograph 10 such that a modulation envelope may be predetermined to provide the requisite flow modulation that will facilitate, if not ensure, a successful ignition even under worst case conditions.

In a further aspect of the present invention, in the ignition of a FID, the make-up fluid flow is discontinued during a portion of the ignition sequence and then resumed after the flame is lit.

In a still further aspect of the present invention, in the ignition of a FID, the first fluid flow is discontinued during a portion of the ignition sequence and then resumed after the flame is lit.

In the preferred embodiment of the chromatograph 10, detector 24 is provided as a plurality of separately located detectors, e.g., a front detector and a back detector. Also in the preferred embodiment, the first detector fluid is provided as hydrogen gas. FIG. 4 illustrates a first preferred ignition sequence that is pertinent to the operation of the chromatograph 10 when one such detector 24 is provided in the form of an FID. In the preferred embodiment, each of the first, second, and third delay periods are approximately 2–3 seconds. FIG. 5 illustrates a second preferred ignition sequence that is pertinent to the operation of the chromatograph 10 when one such detector 24 is provided in the form of an FPD. In the preferred embodiment, each of the first, second, and third delay periods are approximately 1–2 seconds.

EXPERIMENTAL RESULTS

The advantages of the above-described embodiments were demonstrated in a series of ignition repeatability experiments performed on a test apparatus that included a FID mounted in a Hewlett-Packard HP5890 gas chromatograph. Pneumatic control was provided according to the non-EPC configuration illustrated in FIG. 2. Consistent ignition was found to occur according to certain criteria, as will now be described.

One modulation frequency that was found to satisfy these criteria in the chromatograph under test was 0.5 cycles/sec.

A slow duty cycle was found to be preferable because the time demands on the firmware in the computer 22 are lessened and any differences in valve actuation speed are less likely to affect the success of the ignition. Based on the test data, the preferred duty cycle started at 10% and was stepped through several duty cycles until at least 60%, at which point the relevant valve can remain full-on.

Adding a pneumatic volume between the valve 227V and the frit 227F was found to reduce the necessary frequency of actuation and, in addition, increase the range of duty cycling at which the flame will ignite. A volume of 1500 mm$^3$ was found to be the preferred amount.

FIGS. 6–9 illustrate the test results that indicate the effect of certain operating conditions in the chromatograph upon ignition, according to a relationship between flow duty cycle and modulation frequency. In each instance, a successful ignition was found to occur within one or more particular modulation envelopes, each of which relate a range of flow duty cycles and modulation frequencies. The illustrated modulation envelopes are provided as examples of modulation envelopes that were particularly successful is achieving consistent ignition in the FID of the test apparatus, and in no way should be considered limiting.

Figure 6:
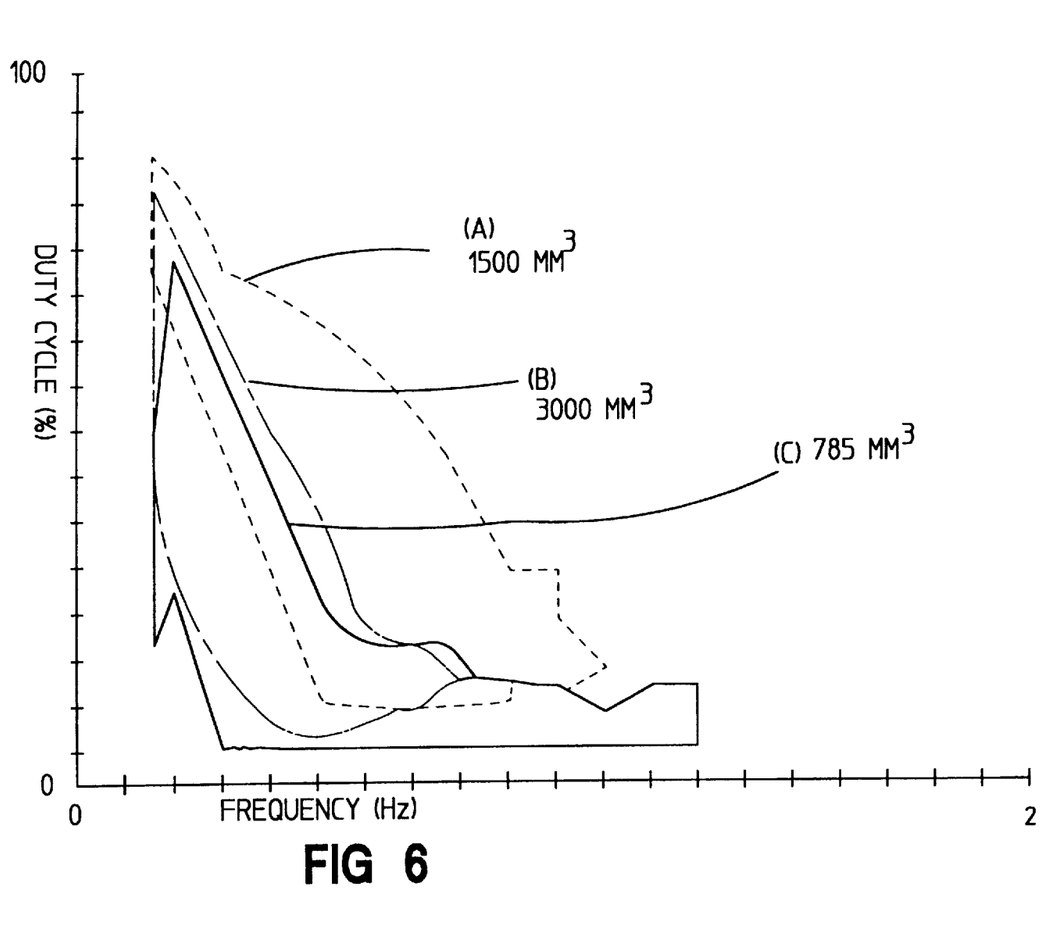
FIGS. 6–9 are graphical representations of successful conditions for establishing ignition in an experimental test of a flame-based detector operated according to the embodiment in FIG. 3, in accordance with the operation and benefit of an inventive feature of the present invention.

FIG. 6 shows first (A), second (B), and third (C) modulation envelopes realized in the aforementioned test apparatus according to a variation in pneumatic volume. The response curves (A), (B), and (C) correspond to the pneumatic volume being implemented as 1500 mm$^3$, 3000 mm$^3$, and 785 mm$^3$ respectively.

Figure 7:
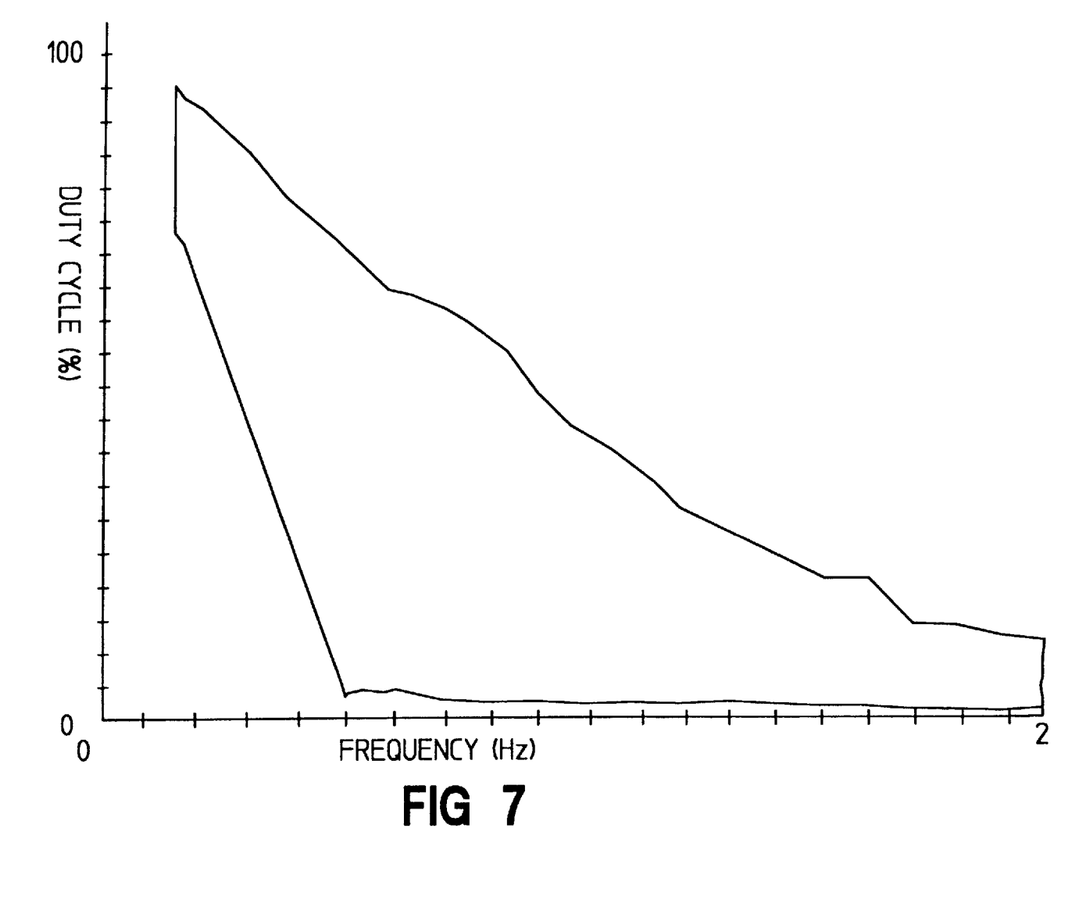

FIG. 7 shows a modulation envelope realized in the aforementioned test apparatus according to an interruption in make-up gas during the ignition sequence.

Figure 8:
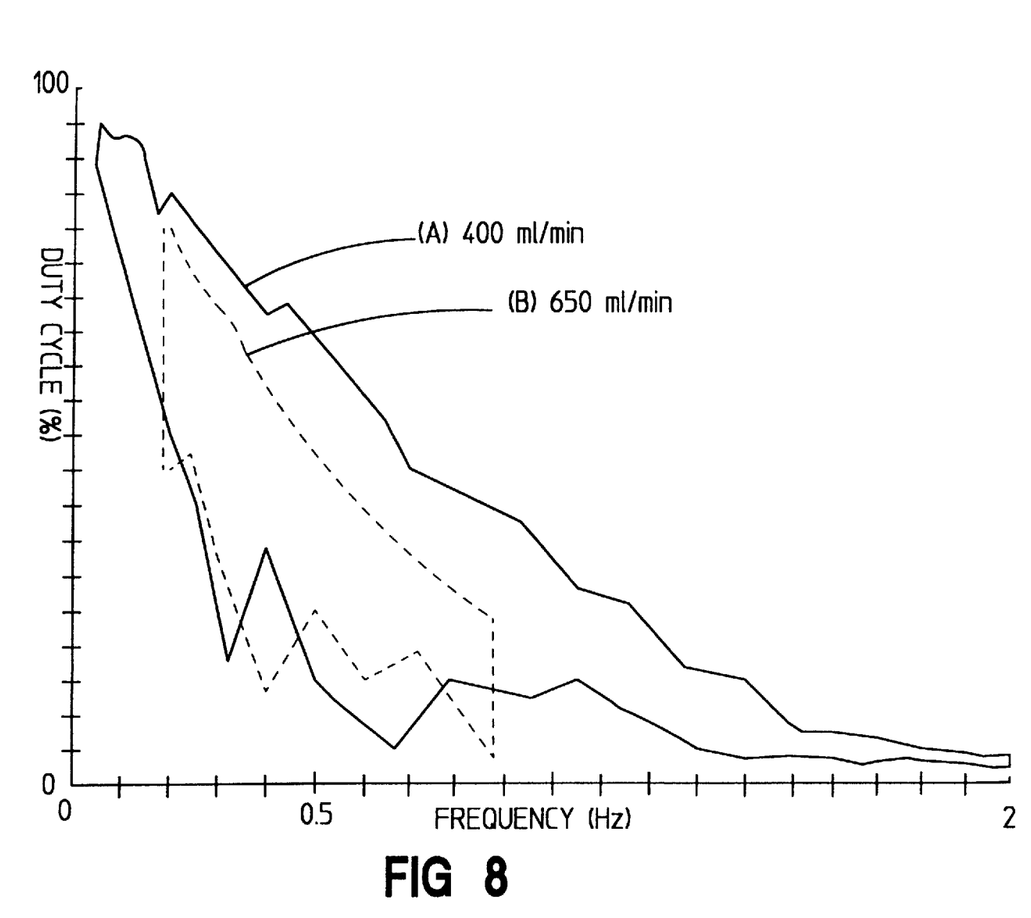

FIG. 8 shows first (A) and second (B) modulation envelopes realized in the aforementioned test apparatus according to differing air flow rates during the ignition sequence. The first and second response curves (A) and (B) correspond to the air flow rates being implemented as 400 milliliters/minute and 650 milliliters/minute, respectively.

Figure 9:
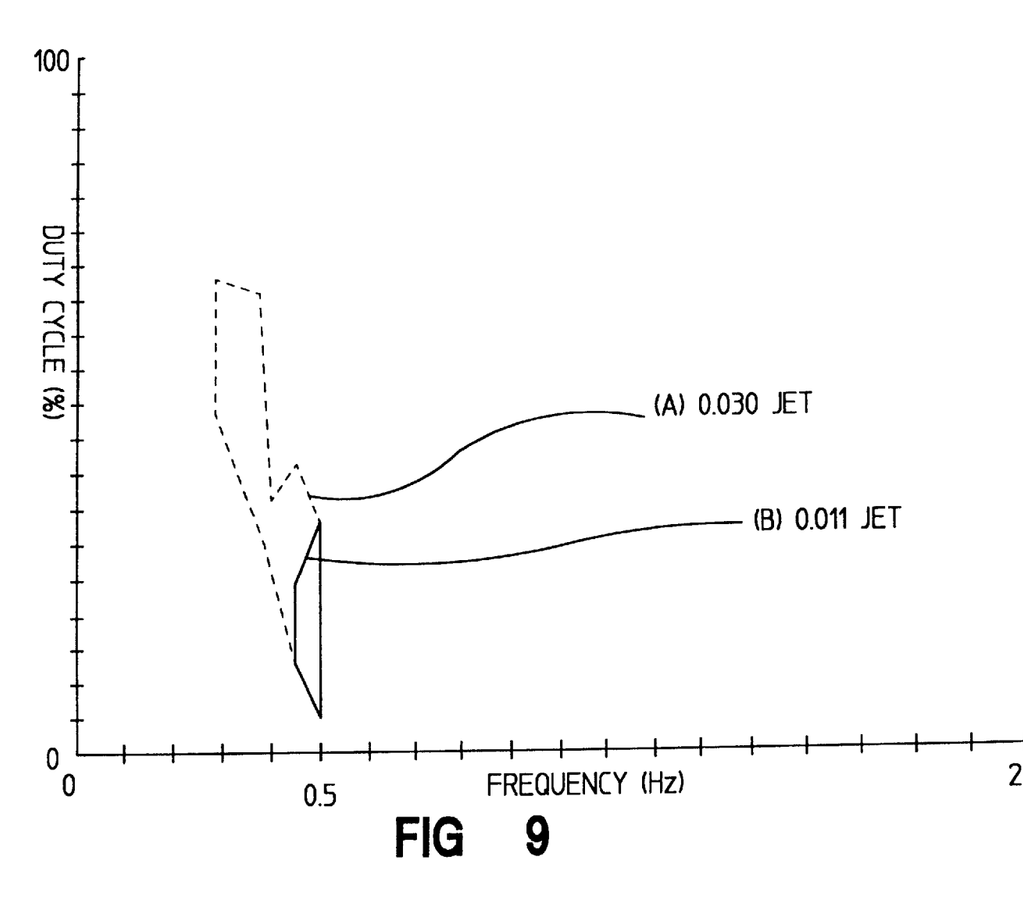

FIG. 9 shows first (A) and second (B) modulation envelopes realized in the aforementioned test apparatus according to differing jet orifice sizes that were used during the ignition sequence. The first and second response curves (A) and (B) correspond to the jet orifice being implemented as 0.030 inches and 0.011 inches, respectively. FIG. 9 illustrates at least two worst case ignition conditions.

ADVANTAGES OF THE INVENTION

By satisfying the ignition flow requirements via valve modulation rather than diverting fluid flow, the preferred embodiment may be constructed without a diverter valve and the associated costs of tubing and fittings, additional assembly labor, and machining of parts. Reliability and ease of use are increased.

The presence of make-up gas and/or carrier gas, each of which undermines successful ignition by diluting the hydrogen and oxygen in the fluid mixture and by cooling the igniter, may be eliminated during a portion of the ignition sequence.

In contrast to systems constructed according to the prior art, a successful ignition in the preferred embodiment is not as subject to manufacturing production variations. Heretofore, a normal variation in, for example, the gas source pressure, which may stray out of the range required by an operating condition for proper ignition would cause the operator to experiment with differing source pressures to try to find a reliable operating region. In the preferred embodiment, the first or second detector fluid flow is modulated during the ignition sequence and therefore will pass through the optimum fluid mixture that facilitates ignition. The modulation is automatically effected during the ignition sequence, in a manner not generally noticeable by the operator, thereby ensuring a reliable flame ignition.

Although the invention has been described with reference to the above-described preferred embodiments, variations and modifications are contemplated as being within the scope and spirit of the present invention.

What is claimed is:

1. An analytical method for detecting the presence of an analyte in a sample fluid, comprising the steps of:

providing a selected flow of at least one of a plurality of detector fluids, said plurality including a first detector fluid and a second detector fluid, determining flow modulation criteria that facilitate ignition;

generating an electronic control signal; and modulating, in response to the electronic control signal, said selected flow;

providing a flame-based detector for receiving the sample fluid and the modulated selected flow;

wherein said modulation in the selected flow is provided according to the predetermined flow modulation criteria and wherein said control signal is applied in a predetermined ignition sequence wherein said modulated flow is effected according to a continuous transition from a first predetermined flow rate to a second predetermined flow rate and according to said flow modulation criteria.

2. The analytical method of claim 1, wherein the flame-based detector is a flame ionization detector, the first detector fluid is hydrogen, and the flow modulation is applied to the first detector fluid.

3. The analytical method of claim 1, wherein the flame-based detector is a flame photometric detector, the second detector fluid is air, and the flow modulation is applied to the second detector fluid.

4. The analytical method of claim 1, wherein the predetermined flow modulation criteria are provided according to a programmable table.

5. The analytical method of claim 1, wherein the step of providing the flame-based detector further comprises the steps of:

providing a fluid mixing structure for receiving the plurality of detector fluids so as to provide a fluid mixture;

providing an igniter capable of heating of the fluid mixture to produce an ignition condition;

providing a collector electrode for receiving the ion current; and providing a fluid-directing structure for aligning the igniter and the collector electrode in a spaced relationship and for directing the fluid mixture so as to contact the igniter and the collector electrode.

6. The analytical method of claim 1, wherein the first and second predetermined flow rates are provided according to a predetermined flow modulation envelope.

7. The analytical method of claim 1, wherein the step of modulating the selected flow is provided according to at least one of a flow duty cycle and a flow modulation frequency.

8. The analytical method of claim 1, wherein the step of modulating the selected flow is provided according to a continuous ramp between the first predetermined flow rate and the second predetermined flow rate.

* * * * *